US008628946B2

(12) United States Patent
Wald et al.

(10) Patent No.: US 8,628,946 B2

(45) Date of Patent: Jan. 14, 2014

(54) PHL P 5A DERIVATIVES HAVING REDUCED ALLERGENEITY AND RETAINED T-CELL REACTIVITY

(75) Inventors: Martin Wald, Hamburg (DE); Oliver Cromwell, Suesel-Fassendorf (DE); Andreas Nandy, Hamburg (DE); Helga Kahlert, Hamburg (DE); Bernhard Weber, Hamburg (DE); Helmut Fiebig, Schwarzenbek (DE)

(73) Assignee: Merck Patent GmbH, Darmstadt (DE)

( * ) Notice: Subject to any disclaimer, the term of this patent is extended or adjusted under 35 U.S.C. 154(b) by 1635 days.

(21) Appl. No.: 10/559,272

(22) PCT Filed: May 6, 2004

(86) PCT No.: PCT/EP2004/004848

§ 371 (c)(1),
(2), (4) Date: Dec. 2, 2005

(87) PCT Pub. No.: WO2004/108758

PCT Pub. Date: Dec. 16, 2004

(65) Prior Publication Data

US 2010/0158955 A1 Jun. 24, 2010

(30) Foreign Application Priority Data

Jun. 4, 2003 (DE) .................................. 103 25 508

(51) Int. Cl.
*C12N 1/00* (2006.01)

(52) U.S. Cl.
USPC .......................................................... 435/243

(58) Field of Classification Search
None
See application file for complete search history.

(56) References Cited

U.S. PATENT DOCUMENTS 5,840,316 A * 11/1998 Singh et al. ................ 424/275.1
2002/0064530 A1 5/2002 Roncarolo et al.

FOREIGN PATENT DOCUMENTS

DE 197 13 001 A 10/1998
DE 199 18 682 A 10/2000
WO WO 03/025009 A 3/2003

OTHER PUBLICATIONS

Ngo et al. 'Computational Complexity, Protein Structure Prediction, and the Levinthal Paradox'. The Protein Folding Problem and Tertiary Structure Prediction. Ed° K. Merz and S. Le Grand. Boston: Birkhauser, 1994.491-495.*

Blumenthal et al, in Allergens and Allergen Immunotherapy, 3rd edition, 2004, pp. 37-51.*

Winther et al. 'Allergen-specific immunotherapy in birch- and grass-pollen-allergic rhinitis. II. Side-effects.' Allergy. 55(9):827-835, 2000.*

Muller et al. 'Mapping of T-cell epitopes of Phl p. 5: evidence for crossreacting and non-crossreacting T-cell epitopes withink Phl p 5 isoallergens.' Clin. Exp. Allerg. 28:1538-1548, 1998.*

Bufe et al. 'Major allergen Phl p Va (timothy grass) bears at least two different IgE-reactive epitopes.' J. Allergy Clin Immunol. 94:173-181, 1994.*

Ong et al. 'Mapping of the antigenic and allergenic epitopes of Lol p VB using gene fragmentation.' Molec. Immunol. 32(4):295-302, 1995.*

Schramm G et al: Allergen Engineering: Variants of the Timothy Grass Pollen Allergen PH1 p 5b With Reduced IgE-Binding Capacity but Conserved T Cell Reactivity: Feb. 15, 1999; Journal of Immunology, Williams & Wilkins Co., US, pp. 2406-2414, XP002216586, ISSN: 0022-1767.

* cited by examiner

*Primary Examiner* — Suzanne M Noakes
*Assistant Examiner* — Stephen Chong
(74) *Attorney, Agent, or Firm* — Millen, White, Zelano & Branigan, P.C.

(57) ABSTRACT

The present invention relates to the preparation and use of variants of the group 5 allergen of the Pooideae which are characterized by reduced IgE reactivity compared with the known wild-type allergens and at the same time by substantially retained reactivity with T lymphocytes. These hypoallergenic allergen variants can be employed for the specific immunotherapy (hyposensitization) of patients having grass pollen allergy or for the preventative immunotherapy of grass pollen allergies.

14 Claims, 11 Drawing Sheets

Figure 3:
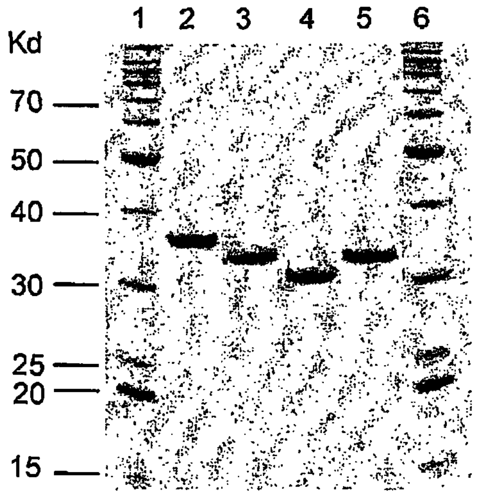

Alignment of relevant regions of Phl p 5a-homologous cDNA sequences of *Pooideae* species: *Lolium perenne* (Lol p), *Poa pratensis* (Poa p) *Triticum aestivum* (Tri a) and *Hordeum vulgare* (Hor v)

Fig. 1

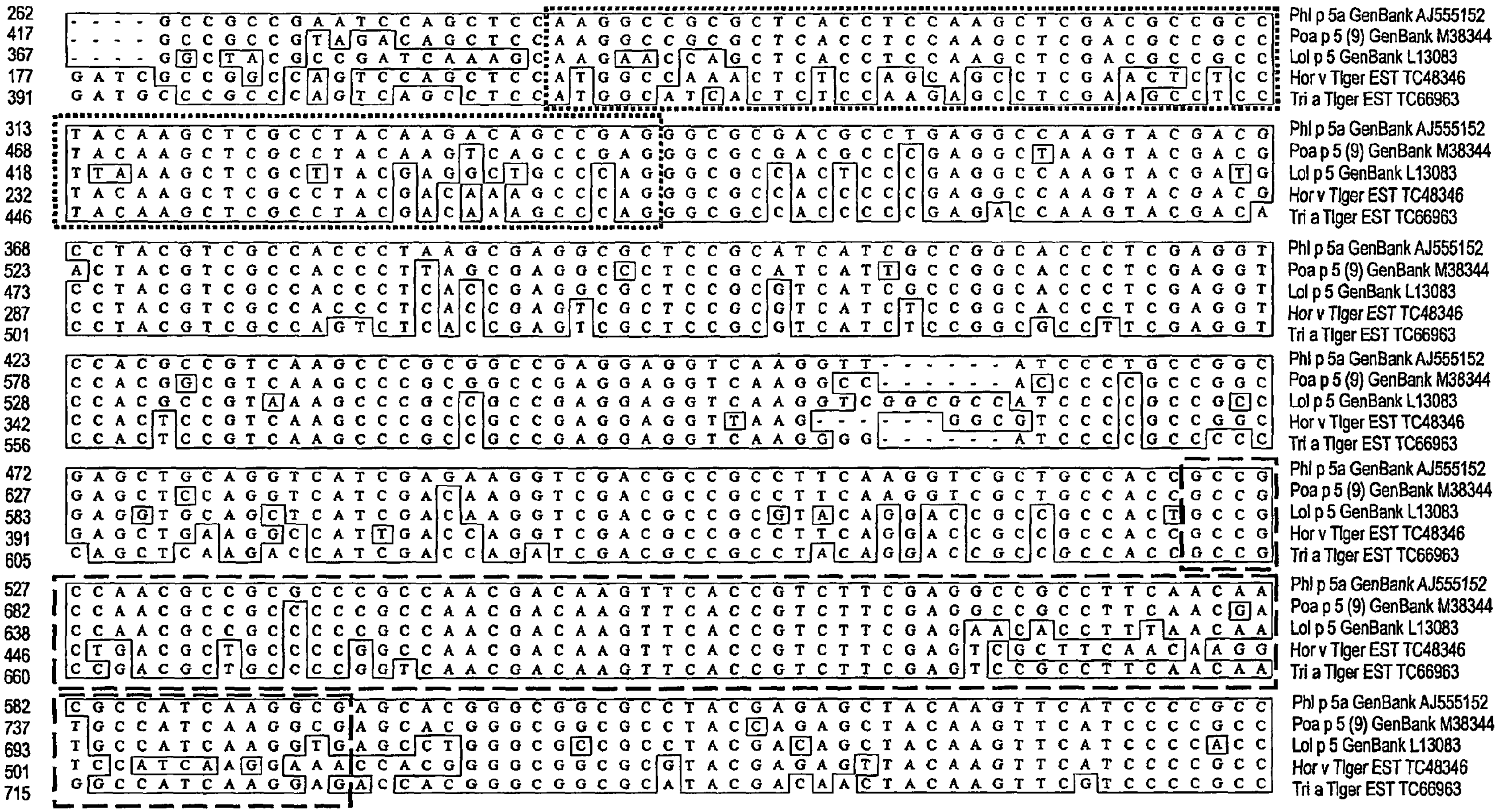

Numbering: nucleotide positions of the DNA insertions

Phl p 5a, Poa p 5 and Lol p 5 sequences: cDNA sequences from "GenBank" database of the *National Center for Biotechnology Information (NCBI)*, Bethesda, USA Hor v and Tri a sequences: EST sequences from EST database of the *Institute for Genomic Research (TIGER)*, Rockville, USA Black borders: sequence identity with Phl p 5a (based on GenBank AJ555152)

*Dotted borders*: deletion corresponding to amino acids 94-113 (based on GenBank AJ555152)

Dashed borders: deletion corresponding to amino acids 175-198 (based on GenBank AJ555152)

Fig. 2a

Fig. 2 { Fig. 2a / Fig. 2b }

**Alignment of Phl p 5a-homologous amino acid sequences (relevant sequence regions, deduced from DNA sequences) of Pooideae species: *Lolium perenne* (Lol p), *Poa pratensis* (Poa p) *Triticum aestivum* (Tri a) and *Hordeum vulgare* (Hor v)**

| | | |
|---|---|---|
| 169 | P P A D K Y R T F V A T F G A A S N K A F A E G L S G E P K | Phl p 5a GenBank AJ555152 |
| 324 | P A A N K Y K T F V A T F G A A S N K A F A E A L S T E P K | Poa p 5 (9) GenBank M38344 |
| 286 | P P A D K Y K T F V E T F G T A T N K A F V E G L A S - - - | Lol p 5 GenBank L13083 |
| 82 | P P A D K Y K T F E A T F A A A S N K A F A E V L K G A A T | Hor v TIger EST TC48346 |
| 296 | P P A D K Y K T F E A T F S A A S N X A F A D V L K A A A S | Tri a TIger EST TC66963 |
| 259 | G - - A A E S S S K A A L T S K L D A A Y K L A Y K T A E G | Phl p 5a GenBank AJ555152 |
| 414 | G - - A A V D S S K A A L T S K L D A A Y K L A Y K S A E G | Poa p 5 (9) GenBank M38344 |
| 367 | - - - G Y A D Q S K N Q L T S K L D A A L K L A Y E A A Q G | Lol p 5 GenBank L13083 |
| 172 | G Q I A G Q S S S M A K L S S S L E L S Y K L A Y D K A Q G | Hor v TIger EST TC48346 |
| 386 | G Q M P A Q S A S M A S L S K S L E A S Y K L A Y D K A Q G | Tri a TIger EST TC66963 |
| 343 | A T P E A K Y D A Y V A T L S E A L R I I A G T L E V H A V | Phl p 5a GenBank AJ555152 |
| 498 | A T P E A K Y D D Y V A T L S E A L R I I A G T L E V H G V | Poa p 5 (9) GenBank M38344 |
| 448 | A T P E A K Y D A Y V A T L T E A L R V I A G T L E V H A V | Lol p 5 GenBank L13083 |
| 262 | A T P E A K Y D A Y V A T L T E S L R V I S G T L E V H S V | Hor v TIger EST TC48346 |
| 476 | A T P E T K Y D T Y V A S L T E S L R V I S G A F E V H S V | Tri a TIger EST TC66963 |
| 433 | K P A A E E V K V - - I P A G E L Q V I E K V D A A F K V A | Phl p 5a GenBank AJ555152 |
| 588 | K P A A E E V K A - - T P A G E L Q V I D K V D A A F K V A | Poa p 5 (9) GenBank M38344 |
| 538 | K P A A E E V K V G A I P A A E V Q L I D K V D A A Y R T A | Lol p 5 GenBank L13083 |
| 352 | K P A A E E V K - - G V P A G E L K A I D Q V D A A F R T A | Hor v TIger EST TC48346 |
| 566 | K P A A E E V K G X X I P A P Q L K T I D Q I D A A Y R T A | Tri a TIger EST TC66963 |

Fig. 2b

| | | |
|---|---|---|
| 517 | A T A A N A A P A N D K F T V F E A A F N N A I K A S T G G | Phl p 5a GenBank AJ555152 |
| 672 | A T A A N A A P A N D K F T V F E A A F N D A I K A S T G G | Poa p 5 (9) GenBank M38344 |
| 628 | A T A A N A A P A N D K F T V F E N T F N N A I K V S L G A | Lol p 5 GenBank L13083 |
| 436 | A T A A D A A P A N D K F T V F E S L Q Q G P S R K P R G G | Hor v TIger EST TC48346 |
| 650 | A T A A D A A P V N D K F T V F E S A F N K A I K E T T G G | Tri a TIger EST TC66963 |
| 607 | A Y E S Y K F I P A L E A A V K Q A Y A A T V A T A P E V K | Phl p 5a GenBank AJ555152 |
| 762 | A Y Q S Y K F I P A L E A A V K Q S Y A A T V A T A P A V K | Poa p 5 (9) GenBank M38344 |
| 718 | A Y D S Y K F I P T L V A A V K Q A Y A A K Q A T A P E V K | Lol p 5 GenBank L13083 |
| 526 | A Y E S Y K F I P A L E A A V K Q A Y A A T V A A A P E V K | Hor v TIger EST TC48346 |
| 740 | A Y D N Y K F V P A L E S A V K Q A Y A A T V A S A P E V K | Tri a TIger EST TC66963 |
| 697 | Y T V F E T A L K K A I T A M S E A Q K A A K P A A A A T A | Phl p 5a GenBank AJ555152 |
| 852 | Y T V F E T A L K K A I T A M S Q A Q K A A K P A A A A T G | Poa p 5 (9) GenBank M38344 |
| 808 | Y T V S E T A L K K A V T A M S E A E K E A T P A A A A T A | Lol p 5 GenBank L13083 |
| 616 | F T V F Q T A L S K A I N A M T Q A G K V A K P A A A A T A | Hor v TIger EST TC48346 |
| 830 | Y A V F Q A A L S K A I N A M V E A E K D A G A A A A G G Y | Tri a TIger EST TC66963 |

Numbering: nucleotide positions of the DNA insertions

**Phl p 5a, Poa p 5 and Lol p 5 sequences: cDNA sequences from "GenBank" database of the *National Center for Biotechnology Information (NCBI)*, Bethesda, USA**

**Hor v and Tri a sequences: EST sequences from EST database of the *Institute for Genomic Research (TIGER)*, Rockville, USA**

Black borders: sequence identity with Phl p 5a (based on GenBank AJ555152)
Dotted borders: deletion corresponding to amino acids 94-113 (based on GenBank AJ555152)
Dashed borders: deletion corresponding to amino acids 175-198 (based on GenBank AJ555152)

SDS-PAGE of purified deletion mutants in the form of histidine fusion proteins

1) Marker
2) rPhl p 5a wt (His)
3) Phl p 5a DM-Δ94-113 (His)
4) Phl p 5a DM-Δ94-113, 175-198 (His)
5) Phl p 5a DM-Δ175-198 (His)
6) Marker

SDS-PAGE of the purified non-fusion proteins Phl p 5a DM-Δ94-113, 175-198 and rPhl p 5a wt (top) and identity test with αPhl p 5 antibodies (bottom)

αPhl p 5 mAb Apha-1D11 binds region 175-198 (only rPhl p 5a wt is positive)

αPhl p 5a mAb Apha-3B2 binds a joint epitope of the two Phl p 5a molecules (both proteins positive)

(mAb: monoclonal antibody)

Analytical SEC of deletion mutant Phl p 5a DM-Δ94-113, 175-198 and of recombinant wild type Phl p 5a (purified non-fusion proteins)

Column: Superdex 75 HR10/ 30 (Amersham Biosciences, Uppsala, Sweden)
Eluent: PBS
Arrow: exclusion volume

Non-denaturing isoelectric focusing of deletion mutant Phl p 5a DM-Δ94-113, 175-198 and of recombinant wild type Phl p 5a (purified non-fusion proteins)

pI rPhl p 5a wt = 8.7
pI rPhl p 5a DM-Δ94-113, 175-198 = 6.4

Strip test for checking the IgE binding ability of Phl p 5a deletion mutants (non-denaturing)

P: sera of clinically defined grass pollen allergy sufferers

Determination of the reduced IgE reactivity of Phl p 5a deletion mutants by means of the EAST inhibition test with two representative single sera (a and b) and a serum pool (c)

Determination of the hypoallergeneity of Phl p 5a deletion mutant Phl p 5a DM-Δ94-113, 175-198 by means of the basophil activation test with basophils of six different grass pollen allergy sufferers (P)

PHL P 5A DERIVATIVES HAVING REDUCED ALLERGENEITY AND RETAINED T-CELL REACTIVITY

This application is a U.S. National Stage application under §371 of the International application PCT/EP04/04848, filed May 6, 2004, which is incorporated by reference herein in its entirety.

The present invention relates to the preparation and use of variants of the group 5 allergen of the Pooideae which are characterised by reduced IgE reactivity compared with the known wild-type allergens and at the same time by substantially retained reactivity with T lymphocytes.

These hypoallergenic allergen variants can be employed for the specific immunotherapy (hyposensitisation) of patients having grass pollen allergy or for the preventative immunotherapy of grass pollen allergies.

A preferred embodiment of the invention relates to variants of the major allergen Phl p 5a from the pollen of timothy grass (*Phleum pratense*).

BACKGROUND OF THE INVENTION

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are liberated from sources of various origin, such as plant pollen, mites, cats or dogs. Up to 40% of these type 1 allergy sufferers in turn exhibit specific IgE reactivity with grass pollen allergens (Freidhoff et al., 1986, J. Allergy Clin. Immunol. 78, 1190-2002).

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens depending on the relative frequency with which the individual allergen molecules react with the IgE antibodies of allergy sufferers.

In the case of timothy grass (*Phleum pratense*), Phl p 1 (Petersen et al., 1993, J. Allergy Clin. Immunol. 92: 789-796), Phl p 5 (Matthiesen and Löwenstein, 1991, Clin. Exp. Allergy 21: 297-307; Petersen et al., 1992, Int. Arch. Allergy Immunol. 98: 105-109), Phl p 6 (Petersen et al., 1995, Int. Arch. Allergy Immunol. 108, 49-54). Phl p 2/3 (Dolecek et al., 1993, FEBS 335 (3), 299-304), Phl p 4 (Haavik et al., 1985, Int. Arch. Allergy Appl. Immunol. 78: 260-268; Valenta et al., 1992, Int. Arch. Allergy Immunol. 97: 287-294, Fischer et al., 1996, J. Allergy Clin. Immunol. 98: 189-198) and Phl p 13 (Suck et al., 2000, Clin. Exp. Allergy 30: 324-332; Suck et al., 2000, Clin. Exp. Allergy 30: 1395-1402) have hitherto been identified as major allergens.

The dominant major allergens of timothy grass (*Phleum pratense*) are Phl p 1 and Phl p 5, with Phl p 5 occurring in two forms 5a and 5b which differ in respect of their molecular weight and are encoded by independent genes. The deduced amino acid sequences both of Phl p 5a and also of Phl p 5b have been determined by means of the recombinant DNA technique. Phl p 5a is a protein of about 32 kDa and reacts with the IgE antibodies of 85-90% of grass pollen allergy sufferers. Phl p 5a exists in a series of homologous variants which differ from one another through point mutations and probably correspond to different allelic forms. The pollen of related grass species, such as, for example, *Lolium perenne, Poa pratensis* inter alia, contains allergens which are homologous with that of Phl p 5a and together are known as group 5 allergens. The high structural homology of these group 5 allergens of grass species causes correspondingly high cross reactivity of the molecules with the IgE antibodies of grass pollen allergy sufferers.

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102 (4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with recombinant expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed T helper cell equilibrium in allergy sufferers is treatment with expressible DNA which encodes for the relevant allergens (immunotherapeutic DNA vaccination). Initial experimental evidence of allergen-specific influencing of the immune response by a DNA vaccine of this type has been furnished in rodents by injection of allergen-encoding DNA (Hsu et al., 1996, Nature Medicine 2 (5): 540-544).

The object on which the present invention is based consisted in the provision of novel variants of the group 5 allergens of the Pooideae at the protein and DNA level which are distinguished by reduced IgE activity at the same time as substantial retention of the T-cell reactivity and are therefore suitable for specific immunotherapy and immunotherapeutic DNA vaccination.

FIGURES

FIG. 1: Alignment of relevant regions of Phl p 5a-homologous cDNA sequences of Pooideae species: *Lolium perenne* (Lol p), *Poa pratensis* (Poa p) *Triticum aestivum* (Tri a) and *Hordeum vulgare* (Hor v)

Numbering: nucleotide positions of the DNA insertions

Phl p 5a (Nucleotides 262-636 of SEQ ID NO: 1), Poa p 5 (SEQ ID NO: 15) and Lol p 5 (SEQ ID NO: 16) sequences: cDNA sequences from "GenBank" database of the National Center for Biotechnology Information (NCBI), Bethesda, USA Hon v (SEQ ID NO: 17) and Tri a (SEQ ID NO: 18) sequences: EST sequences from EST database of the Institute for Genomic Research (TIGR), Rockville, USA Black borders: sequence identity with Phl p 5a (based on GenBank AJ555152)
Dotted borders: deletion corresponding to amino acids 94-113 (based on GenBank AJ555152)
Dashed borders: deletion corresponding to amino acids 175-198 (based on GenBank AJ555152)

FIG. 2: Alignment of Phl p 5a-homologous amino acid sequences (relevant sequence regions, deduced from DNA sequences) of Pooideae species: *Lolium perenne* (Lol p), *Poa pratensis* (Poa p) *Triticum aestivum* (Tri a) and *Hordeum vulgare* (Hor v)
Numbering: nucleotide positions of the DNA insertions
Phl p 5a (Residues 57-262 of SEQ ID NO: 21, Poa p 5 (SEQ ID NO: 19) and Lol p 5 (SEQ ID NO: 201 sequences: cDNA sequences from "GenBank" database of the National Center for Biotechnology Information (NCBI), Bethesda, USA
Hor v (SEQ ID NO: 21) and Tri a (SEQ ID NO: 22) sequences: EST sequences from EST database of the Institute for Genomic Research (TIGR), Rockville, USA
Black borders: sequence identity with Phl p 5a (based on GenBank AJ555152)
Dotted borders: deletion corresponding to amino acids 94-113 (based on GenBank AJ555152)
Dashed borders: deletion corresponding to amino acids 175-198 (based on GenBank AJ555152)

FIG. 3: SDS-PAGE of purified deletion mutants in the form of histidine fusion proteins
1) Marker
2) rPhl p 5a wt (His)
3) Phl p 5a DM-Δ94-113 (His)
4) Phl p 5a DM-Δ94-113, 175-198 (His)
5) Phl p 5a DM-Δ75-198 (His)
6) Marker FIG. 4: SDS-PAGE of the purified non-fusion proteins Phl p 5a DM-D94-113, 175-198 and rPhl p 5a wt (top) and identity test with αPhl p 5 antibodies (bottom)
αPhl p 5 mAb Apha-1D11 binds region 175-198
(only rPhl p 5a wt is positive)
αPhl p 5a mAb Apha-3B2 binds a joint epitope of the two Phl p 5a molecules (both proteins positive)
(mAb: monoclonal antibody)

Figure 5:
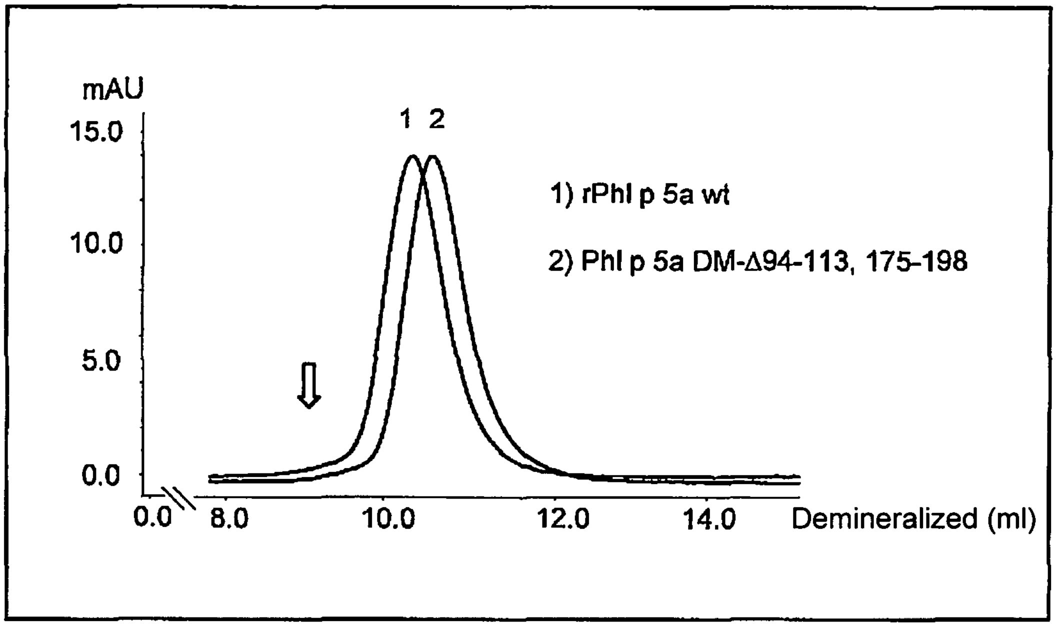

FIG. 5: Analytical SEC of deletion mutant Phl p 5a DM-Δ94-113, 175-198 and of recombinant wild type Phl p 5a (purified non-fusion proteins)
Column: Superdex 75 HR10/30 (Amersham Biosciences, Uppsala, Sweden)
Eluent: PBS
Arrow: exclusion volume FIG. 6: Non-denaturing isoelectric focusing of deletion mutant Phl p 5a DM-Δ94-113, 175-198 and of recombinant wild type Phl p 5a (purified non-fusion proteins)
1) IEF marker
2) rPhl p 5a wt
3) Phl p 5a DM-Δ94-113, 175-198
pI rPhl p 5a wt=8.7
pI rPhl p 5a DM-Δ94-113, 175-198=6.4

Figure 7:
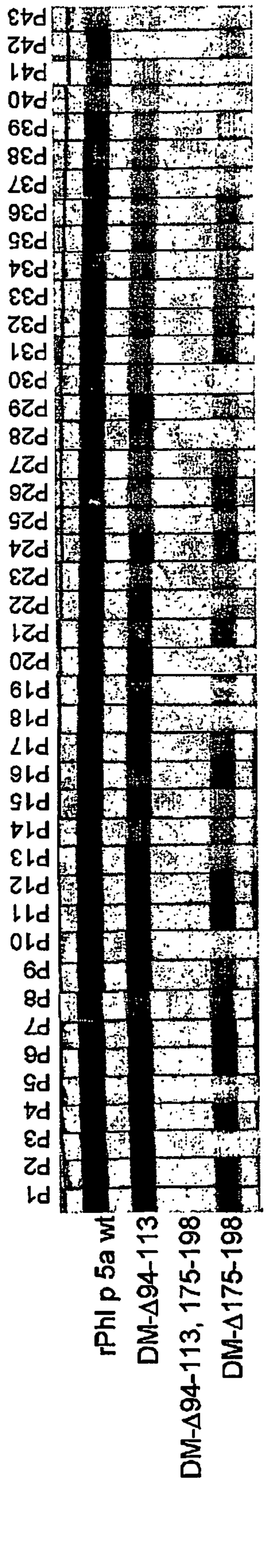
Figure 8:
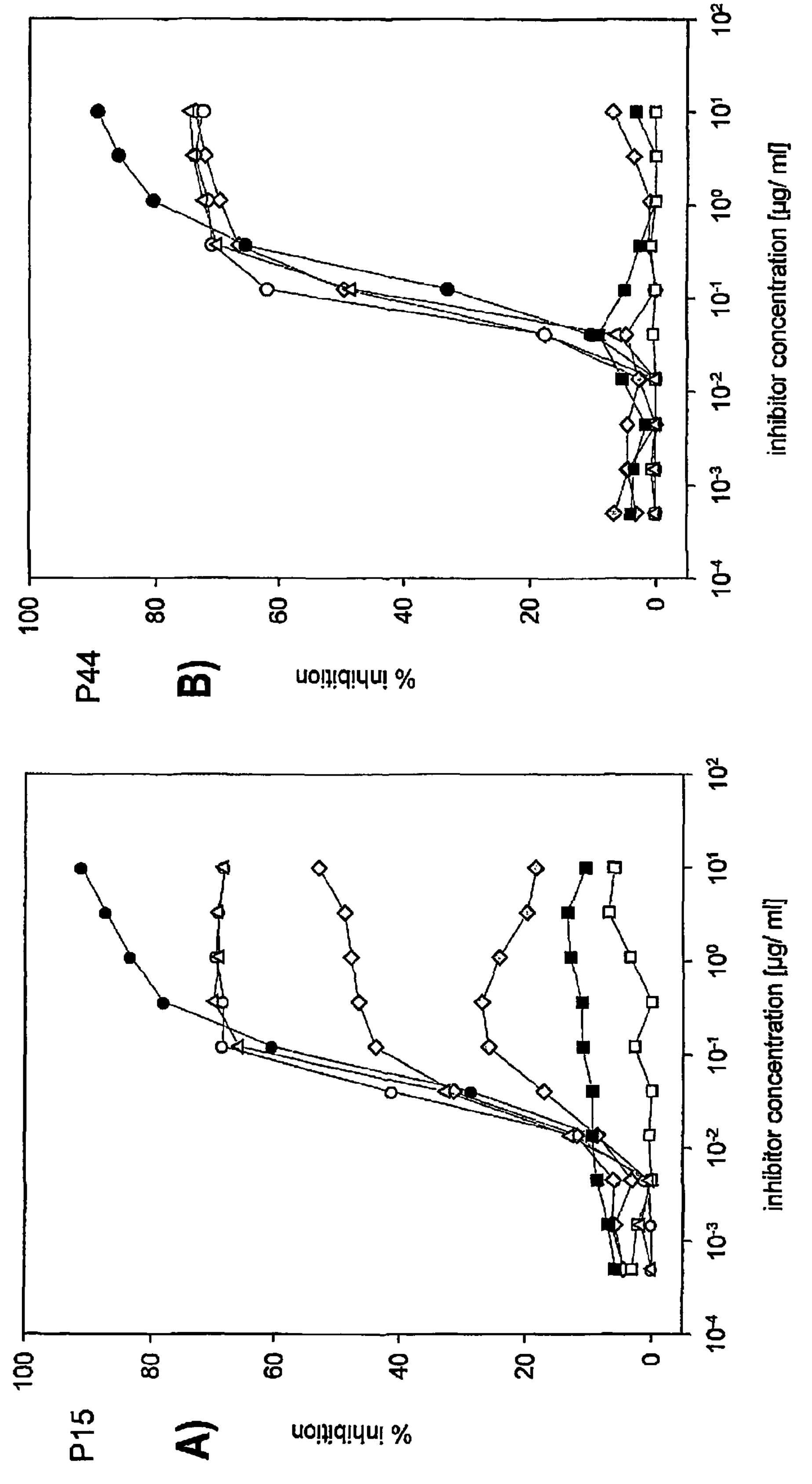
Figure 8:
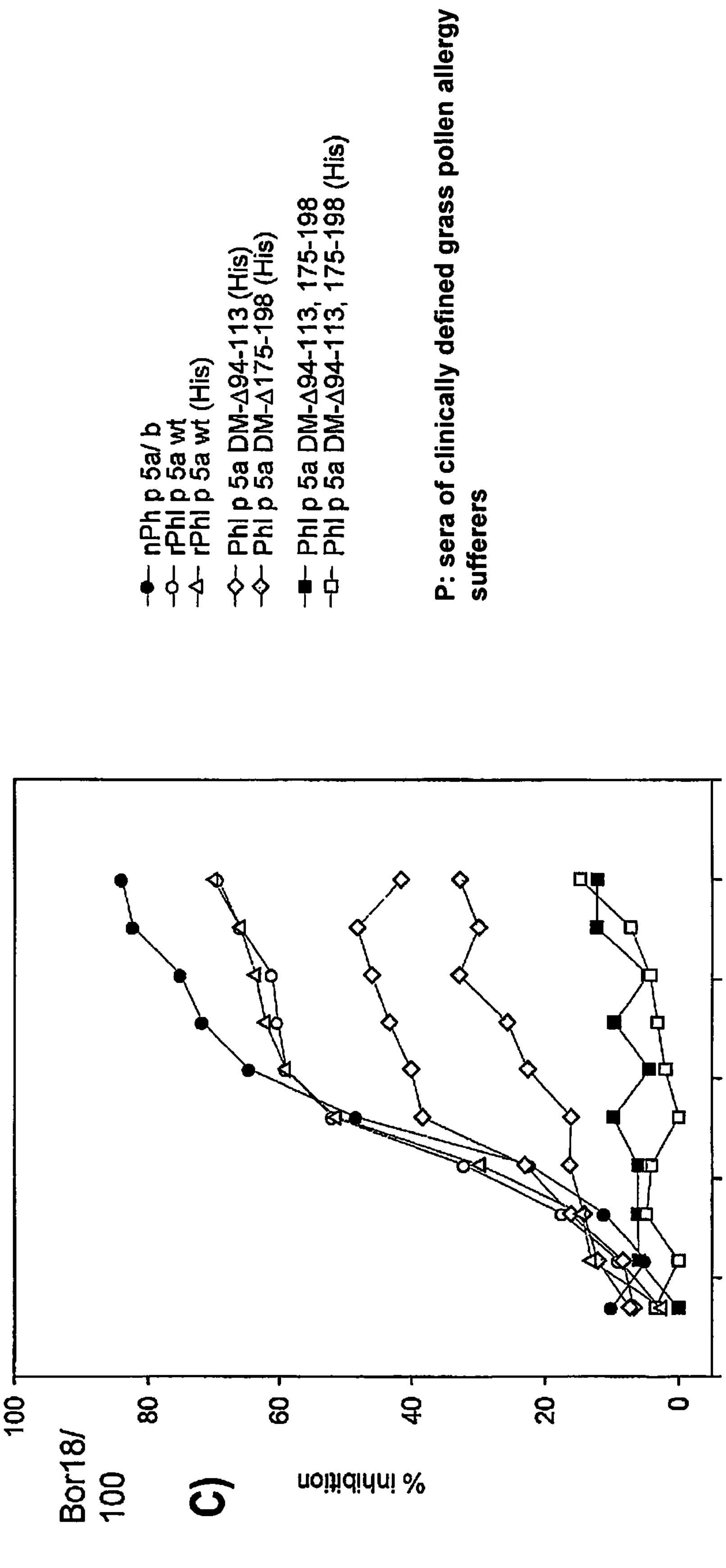
Figure 9:
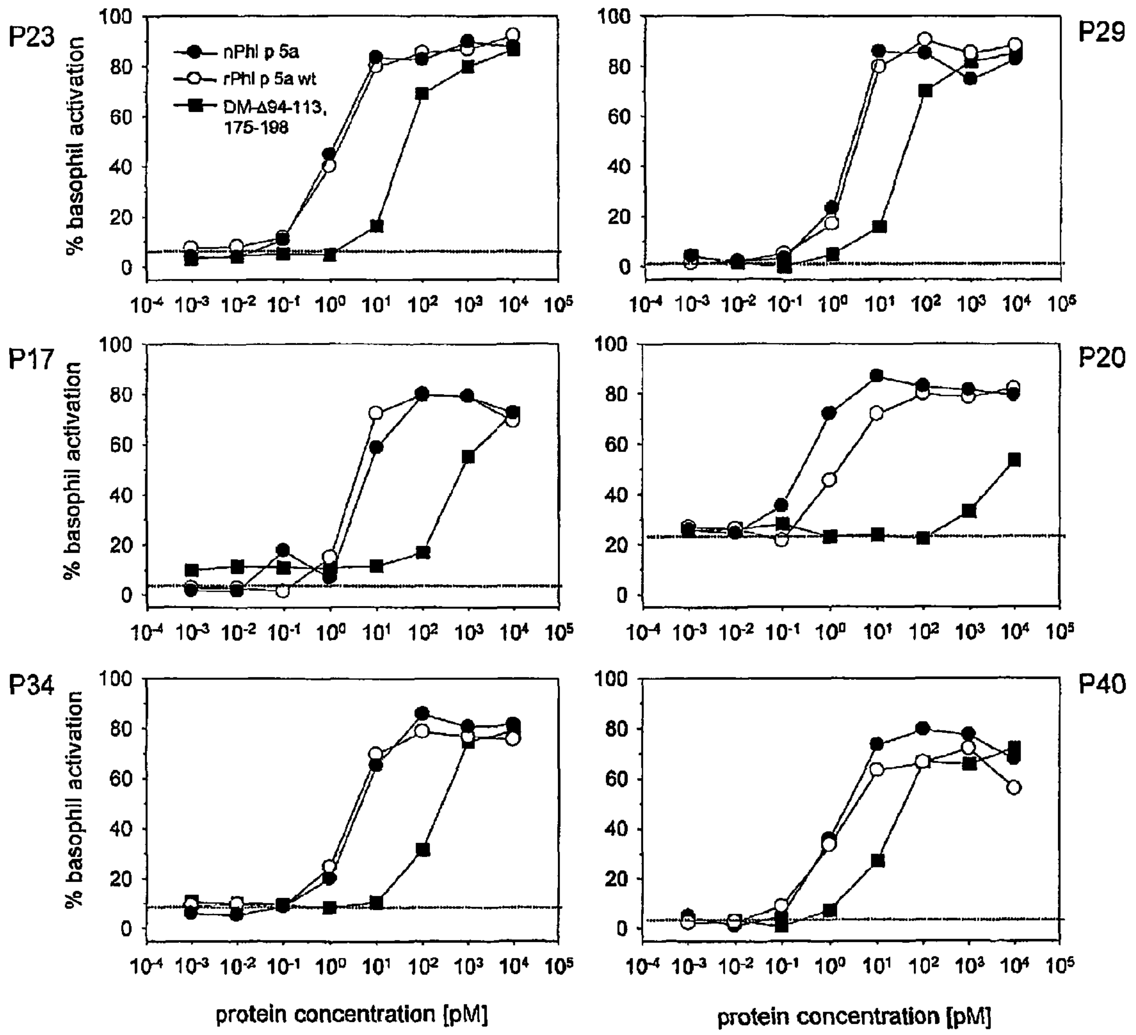

FIG. 7: Strip test for checking the IgE binding ability of Phl p 5a deletion mutants (non-denaturing)
P: sera of clinically defined grass pollen allergy sufferers FIG. 8: Determination of the reduced IgE reactivity of Phl p 5a deletion mutants by means of the EAST inhibition test with two representative single sera (a and b) and a serum pool (c)
—●— nPh p 5a/b
—○— rPhl p 5a wt
—△— rPhl p 5a wt (His)
—◇— Phl p 5a DM-Δ94-113 (His)
—◆— Phl p 5a DM-Δ175-198 (His)
—■— Phl p 5a DM-Δ94-113, 175-198
—□— Phl p 5a DM-Δ94-113, 175-198 (His)
P: sera of clinically defined grass pollen allergy sufferers FIG. 9: Determination of the hypoallergeneity of Phl p 5a deletion mutant Phl p 5a DM-Δ94-113, 175-198 by means of the basophil activation test with basophils of six different grass pollen allergy sufferers (P)

DETAILED DESCRIPTION OF THE INVENTION

Mutagenesis and Cloning of cDNA Sequences

The starting point for the—particularly preferred in accordance with the invention—hypoallergenic Phl p 5a variants is the cDNA of an isoform of wild-type Phl p 5a which has been isolated with the aid of specific primers by polymerase chain reaction (PCR) from the total cDNA of pollen of timothy grass (*Phleum pratense*) (NCBI (National Center for Biotechnology Information, Bethesda, USA) GenBank number AJ555152) (SEQ ID NO 1). The amino acid sequence as per SEQ ID NO 2 has been deduced from the cDNA sequence. Phl p 5a, which consists of 284 amino acids, was expressed cytosolically as soluble protein in *E. coli* and subsequently purified. This recombinant wild-type form of Phl p 5a (rPhl p 5a wt) reacts with monoclonal anti-Phl p 5 antibodies and with IgE antibodies of grass pollen allergy sufferers which have reactivity with natural purified Phl p 5a (nPhl p 5a).

Starting from the described cDNA of rPhl p 5a wt, a series of different deletion variants (deletion mutants) was prepared by restriction/ligation methods and PCR and ligated into the expression vector pProExHTa (Invitrogen, Carlsbad, USA). Sections with a length of 6 to 72 by distributed over the entire sequence of the cDNA molecule were deleted, causing induction of corresponding deletions in the polypeptide chains of the proteins expressed in *E. coli*.

The deletion variants of Phl p 5a were investigated by immunoblot for their binding ability to IgE antibodies of a representative serum pool of grass pollen allergy sufferers.

In this method, surprisingly, two deletion variants of Phl p 5a (Phl p 5a DM-Δ94-113, deletion of amino acids 94-113 and Phl p 5a DM-Δ175-198, deletion of amino acids 175-198 of rPhl p 5a wt) were found, which have reduced binding of IgE antibodies (representative serum pool). These two Phl p 5a deletions served as starting point for the construction of a double deletion mutant containing both effective deletions (Phl p 5a DM-Δ94-113, 175-198).

The construction of Phl p 5a DM-Δ94-113, Phl p 5a DM-Δ175-198 and Phl p 5a DM-Δ94-113, 175-198 by genetic engineering methods and the biochemical and immunological characterisation thereof are described below.

For the construction of deletion variant Phl p 5a DM-Δ94-113 (SEQ ID NO 3, cDNA sequence (795 bp), and SEQ ID NO 4, amino acid sequence (264 aa)), firstly two fragments were prepared starting from the cDNA of rPhl p 5a wt. Fragment "F1-93", encoding for amino acids 1-93 of rPhl p 5a wt, was prepared by PCR with the aid of primers 1 and 5, and fragment "F114-284" was prepared with the aid of primers 4 and 6 (primer sequences see Table 1). Fragments "F1-93" and "F114-284" were employed as matrix in a further PCR using primers 1 and 4, which resulted in amplification of the complete cDNA encoding for deletion variant Phl p 5a DM-Δ94-113. The basis of the connection of fragments "F1-93" and "F114-284" by PCR was a sequence region common to both fragments. This sequence region was formed by amplification of fragment "F114-284" by PCR by means of a particular sense oligonucleotide which contained an additional DNA sequence encoding for amino acids 88-93 in the 5' region (Table 1).

The cDNA sequence encoding for deletion variant Phl p 5a DM-Δ175-198 (SEQ ID NO 5, cDNA sequence (783 bp), and SEQ ID NO 6, amino acid sequence (260 aa)) was generated by restriction and subsequent ligation of two separately prepared cDNA fragments. The 5'-terminal fragment "F1-174" was prepared by PCR with the aid of primers 1 and 2 and the 3'-terminal fragment "F199-284" with the aid of primers 3 and 4. The cDNA fragments were digested with the restriction enzyme SpeI and subsequently ligated (see Table 1). The ligation product was amplified by PCR using primers 1 and 4.

The cDNA of deletion variant Phl p 5a DM-Δ94-113, 175-198 (SEQ ID NO 7, cDNA sequence (723 bp), and SEQ ID NO 8, amino acid sequence (240 aa)) was likewise prepared from two cDNA fragments. The 5'-terminal fragment was generated using primers 1 and 5 and with rPhl p 5a wt-cDNA as matrix, and the 3'-terminal fragment was generated using primers 4 and 6 with Phl p 5a DM-Δ175-198-cDNA as matrix. By means of the common sequence region corresponding to amino acids 88-93 of the rPhl p 5a wt protein, the fragments were connected by a third PCR using primers 1 and 4, and the product was amplified.

The cDNAs encoding for the modified allergens were ligated into the expression vector pProExHT (Invitrogen, Carlsbad, USA) via the EheI and HindIII restriction sites and subsequently sequenced in full.

The immunological cross reactivity of the group 5 allergens of the Pooideae, such as, for example, *Poa pratensis* and *Lolium perenne*, is based on a very similar amino acid sequence. It can be taken as certain that the corresponding genes go back to a common progenitor gene. Homologous sequence regions in the group 5 allergens of the Pooideae exist both for the sequences of deletions Δ94-113 and Δ175-198 of the Phl p 5a wt protein sequence (reference: GenBank AJ555152) and also for the flanking sequence regions thereof. The high homology of the sequence regions in question can be demonstrated both at the DNA level and also at the amino acid sequence level (FIG. 1 and FIG. 2).

TABLE 1

List of the PCR primers employed for the preparation of deletion variants

| Primer | SEQ ID NO | Direction | Sequence (5'→3') |
|---|---|---|---|
| 1 | 9 | sense | gcc gat cta ggc tac ggc ccg gcc |
| 2 | 10 | antisense | aac ata act agt ggc agc gac ctt gaa ggc ggc gtc |
| 3 | 11 | sense | atc ta act agt acg ggc ggc gcc tac gaga |
| 4 | 12 | antisense | aac ata aag ctt tca gac ttt gta gcc acc agt |
| 5 | 13 | antisense | gga gct gga ttc ggc ggc gcc ctt ggg |
| 6 | 14 | sense | gcc gcc gaa tcc agc tcc ggc gcg acg cct gag gcc aag tac gac |

The SpeI restriction sites are indicated by underlining

Expression and Purification of Recombinant Phl p 5a Molecules

The recombinant proteins were expressed as histidine fusion proteins with integrated protease cleavage site (expression vector pProExHT; Invitrogen, Carlsbad, USA) for optional removal of the histidine fusion component (His) in *Escherichia coli* (strain JM109). rPhl p5a wt and the deletion mutants were firstly purified by specific binding of the N-terminal histidine residues to an Ni2+ chelate matrix (immobilised metal ion affinity chromatography, IMAC) and subsequently by preparative gel filtration (size exclusion chromatography, SEC).

The purity of the eluted proteins was monitored by SDS-PAGE and analytical SEC. The results showed that rPhl p 5a wt (His), Phl p 5a DM-Δ94-113 (His); Phl p 5a DM-Δ175-198 (His) and Phl p 5a DM-Δ94-113, 175-198 (His) could be prepared with high purity and in monomeric form (FIG. 3). The identity of the proteins was demonstrated by Phl p 5a-specific monoclonal antibodies.

The checking of the IgE reactivity by means of IgE binding techniques (immunoblotting, strip test, EAST inhibition test and basophil activation test) and the investigation of the T-cell reactivity was in addition carried out with test substances without a histidine fusion component.

Figure 4:
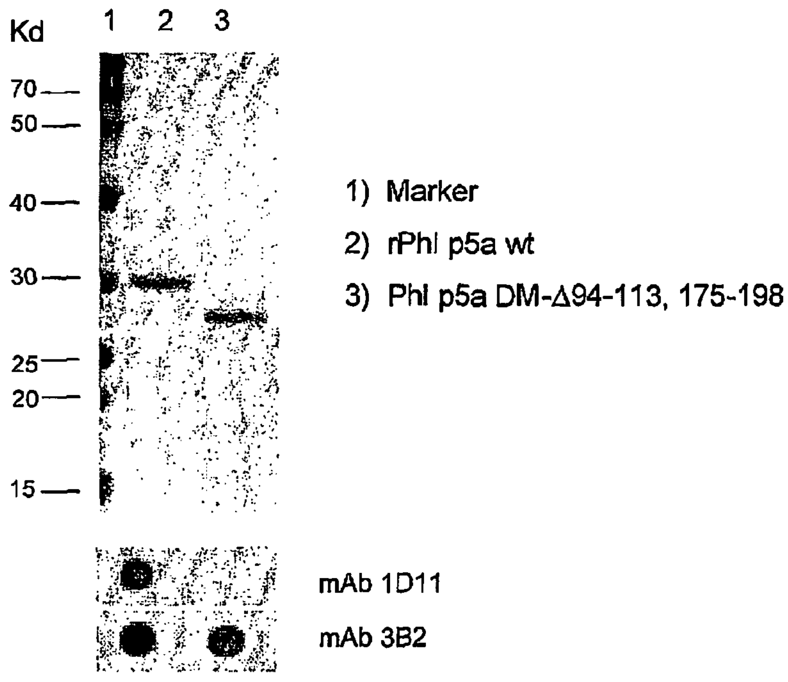
Figure 6:
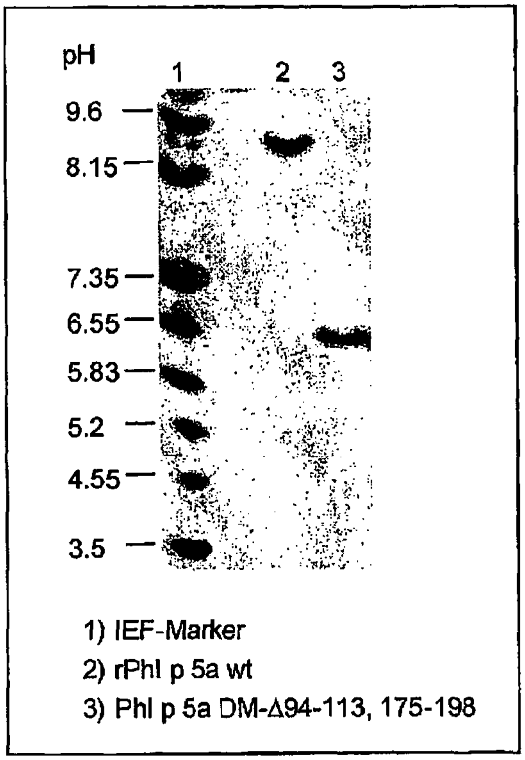

To this end, the deletion variants was prepared in parallel to the comparative protein rPhl p 5a-wt firstly as fusion proteins. However, the histidine fusion component was subsequently cleaved off enzymatically (TEV protease, Invitrogen, Carlsbad, USA), leaving only a glycine as residue of the protease cleavage sequence on the N terminal of the target protein. Both the cleaved-off histidine component and also the protease used for the cleavage were separated off completely by IMAC. After preparative SEC, the purity and conformation of the eluted proteins was checked by SDS-PAGE and analytical SEC, as shown in FIGS. 4 and 5 for rPhl p 5a wt and the mutant Phl p 5a DM-Δ94-113, 175-198 respectively. All proteins were prepared in pure and monomeric form. An investigation by non-denaturing isoelectric focusing (IEF) of the non-fusion proteins always showed high homogeneity with respect to the surface charge (see FIG. 6, illustrative for Phl p 5a DM-Δ94-113, 175-198).

The identity of the recombinant proteins was demonstrated by the monoclonal anti-Phl p 5 antibodies (Allergopharma, Reinbek, Germany) Apha-1D11 or Apha-3B2 (see FIG. 4, illustrative for Phl p 5a DM-Δ94-113, 175-198) and N-terminal sequencing.

Determination of Reduced IgE Binding of the Phl p 5a Deletion Variants

A simple test method for determination of the IgE reactivity of allergenic molecules is investigation of the binding of specific IgE from the sera from allergy sufferers to membrane-bound test proteins by the strip test.

For this purpose, the test substances are bound in the same concentration and amount alongside one another to a strip of nitrocellulose membrane under non-denaturing conditions. A series of such membrane strips can be incubated in parallel with various sera from allergy sufferers. After a washing step, the specifically bound IgE antibodies are rendered visible on the membrane by a colour reaction promoted by an anti-hIgE/alkaline phosphatase conjugate.

The IgE reactivity of the recombinant proteins Phl p 5a wt (His), Phl p 5a DM-Δ94-113 (His), Phl p 5a DM-Δ175-198 (His) and Phl p 5a DM-Δ94-113, 175-198 (His) was investigated comparatively in the strip test using 43 individual sera from grass pollen allergy sufferers (FIG. 7).

All 43 sera from allergy sufferers contained Phl p 5a-specific IgE antibodies which reacted strongly with the natural Phl p 5a (nPhl p 5a, not shown here) and the recombinant equivalent rPhl p 5a wt (His).

Surprisingly, it became clear that the Phl p 5a-specific IgE antibodies of all 43 patient sera did not bind at all to deletion variant Phl p 5a DM-Δ94-113, 175-198 (His) or only did so to a very greatly reduced extent. The reduced IgE binding is attributable both to the deletion Δ94-113 and also to the deletion Δ175-198. Deletion variant Phl p 5a DM-Δ175-198 (His) shows a clearly recognisably reduced IgE binding capacity in this test in 35 of 43 sera from allergy sufferers. In some tests, the influence of the deletion of amino acids 175-198 was so great that IgE binding was virtually completely prevented (Ex.: P3, P20, P28)

The influence of deletion Δ94-113 on the IgE binding reactivity is less pronounced, but likewise clearly visible. Deletion variant Phl p 5a DM-Δ94-113 (His) was bound significantly more weakly by IgE of 19 of the 43 individual sera from allergy sufferers than the reference rPhl p 5a wt (His) (Ex.: P31, P37, P42). However, the reduction in the IgE binding was less drastically pronounced in many individual tests than the reduction caused by Δ175-198.

It is thus clear that both deletions contribute to the reduction in the total IgE binding reactivity of the deletion mutant Phl p 5a DM-Δ94-113, 175-198 (His).

In contrast to the strip test, the EAST inhibition test (enzyme allergosorbent test) allows the investigation of allergen/IgE interactions in solution, enabling interfering masking of epitopes of the test substance by immobilisation on the membrane to be fundamentally excluded. The EAST inhibition test is carried out as follows. Microtitre plates are coated with allergens, here natural Phl p 5 (nPhl p 5a/b, mixture of Phl p 5a and Phl p 5b). After removal of the unbound allergen molecules by washing, the plate is blocked with bovine serum albumin in order to prevent later non-specific binding. IgE antibodies of allergy sufferers, as representative pool of individual sera (serum pool) or as single serum, is incubated in suitable dilution with the allergen-coated microtitre plates. The amount of allergen-bound IgE antibodies is quantified photometrically via an enzyme coupled to a second antibody (anti-hIgE/alkaline phosphatase conjugate) through conversion of a substrate into a coloured end product.

The binding of the IgE antibodies is inhibited substance-specifically by a soluble allergen or the substance to be tested (recombinant modified allergen) depending on the concentration. Immunochemically identical substances show identical inhibition curves.

The reference molecules used in this work were nPhl p 5, rPhl p 5a wt, and the histidine fusion protein rPhl p 5a wt (His). Besides other molecules, the IgE binding of the histidine fusion proteins Phl p 5a DM-Δ94-113 (His), Phl p 5a DM-Δ175-198 (His) and Phl p 5a DM-Δ94-113, 175-198 (His) and that of the non-fusion protein Phl p 5a DM-Δ94-113, 175-198 was investigated by comparison with these references.

FIGS. 8*a-c* show representatively the specific inhibition curves of test substances raised with two individual sera and a serum pool of grass pollen allergy sufferers. nPhl p 5a/b showed the greatest inhibitory effect in all tests (about 80-95% inhibitory effect at a concentration of 10 μg/ml). The inhibitory effect of rPhl p 5a was significantly lower with a maximum inhibition of 70-80%. This effect is caused by the composition of nPhl p 5a/b, which also contains the isoform Phl p 5b in addition to the isoform Phl p 5a. The specific IgE antibodies against Phl p 5b cannot be inhibited by rPhl p 5a wt.

The histidine fusion component showed no effect on IgE binding. This is clear in all tests through the identical inhibition curves of rPhl p 5a wt (His) and rPhl p 5a wt. This demonstrates the validity of tests with histidine fusion proteins.

In general, two groups of patient sera were distinguished with respect to qualitative IgE binding.

The first group is represented by individual serum P15 (FIG. 8*a*). These sera from allergy sufferers contained IgE antibodies whose binding to Phl p 5a was reduced by both deletions, Δ94-113 and Δ175-198. Deletion mutant Phl p 5a DM-Δ94-113 (His) showed only a maximum inhibitory effect of about 50% here, and the deletion mutant Phl p 5a DM-175-198 (His) showed an inhibitory effect of only 20-30%.

The double deletion mutant Phl p 5a DM-Δ94-113, 175-198 (His) was only able to inhibit the binding of IgE antibodies by 0-10% at the highest concentration employed. The use of the non-fusion protein Phl p 5a DM-Δ94-113, 175-198 confirmed this result (0-10% maximum IgE inhibition).

The second group of sera from allergy sufferers, represented by individual serum P44 (FIG. 8*b*), differed from the first group through the fact that the IgE antibodies present in the sera reacted equally well with Phl p 5a DM-Δ94-113 (His) as with the reference rPhl p 5a wt (His) (70-80% maximum inhibition), whereas no or non-detectable amounts of IgE antibodies reacted with Phl p 5a DM-Δ175-198 (His) (0-10% maximum inhibition).

The double deletion mutant Phl p 5a DM-Δ94-113, 175-198 likewise showed a greatly reduced inhibitory effect (0-10%) with this group of sera from allergy sufferers, which was shown both for the fusion protein and also for the fusion component-free protein.

The sera of these allergy sufferers apparently contained IgE antibodies directed principally against epitopes of the C-terminal part of the molecule.

The measurement data of the IgE binding reactivity of IgE antibodies of a serum pool of 20 allergy sufferers underline the importance of the deletions Δ94-113 and Δ175-198 for the reduction in the IgE binding of Phl p 5a (FIG. 8*c*). Both individual deletion mutants, Phl p 5a DM-Δ94-113 (His) and Phl p 5a DM-Δ175-198 (His) show a lower maximum inhibitory effect, of 40-50% and about 30% respectively, than rPhl p 5a wt (about 70%). The double deletion mutant Phl p 5a DM-Δ94-113, 175-198 was only bound very weakly by the IgE antibodies of the serum pool (10-15% maximum inhibition), which, in agreement with the test of 43 allergy sufferers in the strip test, indicates greatly reduced IgE binding reactivity of this Phl p 5a variant in very many, if not all, grass pollen allergy sufferers.

Determination of the Hypoallergeneity of the Deletion Mutants by Basophil Activation Test By means of a basophil activation test, the effects of reduced IgE binding ability of the deletion mutants on the functional effect in the crosslinking of membrane-bound IgE of the effector cells and activation thereof were investigated. The functional reduction in allergeneity was thus measured in a sensitive in-vitro test.

For the basophil activation test, heparinised full blood from grass pollen allergy sufferers is incubated with various concentrations of the test substances. Allergenic substances are able to bind specific IgE antibodies, which are associated with the high-affinity IgE receptors of the basophilic granulocytes.

Crosslinking of the IgE/receptor complexes initiated by the allergen molecules results in signal transduction, which results in degranulation of the effector cells and thus initiation of the allergic reactions in vivo.

In vitro, allergen-induced activation of basophilic immunocytes can be determined by quantification of the expression of a surface protein (CD203c) coupled to signal transduction of the IgE receptor crosslinking (Kahlert et al., Clinical Immunology and Allergy in Medicine Proceedings of the EAACI 2002 (2003) Naples, Italy 739-744). The number of expressed surface proteins on a cell and the percentage of activated cells of a cell pool is measured highly sensitively via the binding of a fluorescence-labelled monoclonal antibody to the surface protein and subsequent analysis by fluorescence-activated flow cytometry.

The reference substances employed here were both purified natural Phl p 5a (nPhl p 5a) and also rPhl p5a wt in parallel with the test substances. The test results of the double deletion mutant Phl p 5a DM Δ94-113, 175-198 with basophils from six test persons are shown as curves in FIG. 9. The test results with basophils from a total of 10 clinically defined allergy sufferers are shown in Table 2.

The A50 values (A50: allergen concentration at 50% of the number of basophils activated to the maximum) of the reference molecules were, varying individually, between ~1.3-15 pM for rPhl p 5a wt and ~0.3-10 pM for nPhl p 5a (Table 2). By contrast, the A50 values of deletion variant Phl p 5a DM Δ94-113, 175-198 were between ~18-8400 pM.

The A50 values determined for the three substances employed were used to determine the allergenic efficacy of deletion variant Phl p 5a DM Δ94-113, 175-198 in relation to the unchanged reference molecules nPhl p 5a and rPhl p5a wt for each test person (Table 2).

The relative allergenic efficacy (Pr, relative potency) of deletion variant Phl p 5a DM Δ94-113, 175-198 was reduced between ~12-5000 fold compared with the reference rPhl p 5a wt or ~16-32000 fold compared with the reference nPhl p 5a (Table 2).

TABLE 2

Determination of the hypoallergeneity of deletion mutant Phl p 5a DM-Δ94-113, 175-198 by means of basophil activation test

| | Test substance $A_{50}$ [pM][a] | | | Pr value[b] Phl p 5a DM-Δ94-113, | Pr value[b] Phl p 5a DM-Δ94-113, |
|---|---|---|---|---|---|
| Donor[c] | nPhl p 5a | rPhl p 5a wt | Phl p 5a DM-Δ94-113, 175-198 | 175-198 relative to rPhl p 5a wt[d] | 175-198 relative to nPhl p 5a[e] |
| P13 | 4.08 | 5.34 | 477.2 | 0.0111 | 0.0085 |
| P17 | 6.44 | 2.68 | 466.6 | 0.0057 | 0.0137 |
| P20 | 0.26 | 1.68 | 8433.0 | **0.0002**[f] | **0.00003**[f] |
| P23 | 1.02 | 1.26 | 39.2 | 0.0321 | 0.0260 |
| P24 | 1.22 | 2.57 | 58.1 | 0.0442 | 0.0209 |
| P28 | 9.43 | 11.35 | 198.2 | 0.0573 | 0.0476 |
| P29 | 1.77 | 2.34 | 33.7 | 0.0694 | 0.0525 |
| P31 | 10.15 | 14.66 | 3967.0 | 0.0037 | 0.0026 |
| P34 | 3.48 | 2.54 | 165.1 | 0.0153 | 0.0211 |
| P40 | 1.08 | 1.45 | 17.5 | **0.0829** | **0.0617** |

[a]Allergen concentration at 50% of the number of basophils activated to the maximum
[b]Relative potency
[c]Clinically defined grass pollen allergy sufferers
[d]Calculated from A50 rPhl p 5a wt/A50 Phl p 5a DM-Δ94-113, 175-198
[e]Calculated from A50 nPhl p 5a/A50 Phl p 5a DM-Δ94-113, 175-198
[f]Bold: minimum and maximum values T-Cell Reactivity T helper lymphocytes react with peptide fragments of the allergens (approx. 12-25 amino acids) formed by enzymatic degradation in antigen-presenting cells (APCs) and are presented to the T-cells after inclusion of the suitable peptides in the individual MHC class II molecules at the surface of the APCs. This allergen-specific activation of the T helper lymphocytes is the prerequisite for subsequent reactions (proliferation, anergy, apoptosis) and for functional differentiation (TH1 and TH2). The influencing of allergen-specific T-lymphocytes by treatment with an allergen or an allergen variant in hyposensitisation is regarded as the key for the therapeutic efficacy.

In order to investigate T-cell reactivity, oligoclonal T-cell lines (TCLs) of Graminae pollen allergy sufferers are established by conventional methods with stimulation by nPhl p5 or rPhl p 5 molecules.

In a proliferation test, the various T-cell lines were stimulated with the reference allergens nPhl p5a and rPhl p5a wt and the double deletion mutant Phl p 5a DM Δ94-113, 175-198. The proliferation rate was determined by the incorporation of [$^3$H] thymidine by conventional methods.

TABLE 3

Determination of the T-cell reactivity of deletion mutant Phl p 5a DM-Δ94-113, 175-198 by means of proliferation tests with Phl p 5-specific T-cell lines (TCLs)

| | | Stimulation index[a] | | |
|---|---|---|---|---|
| Donor[b] | TCL | nPhl p 5a | rPhl p 5a wt | Phl p 5a DM-Δ94-113, 175-198 |
| A | 3.2 | 9.8 | 4.9 | 4.4 |
| B | 8.2 | 21.0 | 15.5 | 13.3 |
| C | 11.2 | 5.2 | 4.7 | 7.2 |
| C | 11.3 | 3.3 | 2.9 | 3.5 |
| C | 11.43 | 3.0 | 3.9 | 2.6 |
| D | 19.1 | 6.5 | 4.7 | 7.5 |
| D | 19.2 | 9.6 | 3.3 | 2.6 |
| E | 23.22 | 21.8 | 29.0 | 20.8 |
| E | 23.50 | 7.5 | 8.4 | 6.6 |
| F | 89.23 | 1.8 | 3.5 | 1.8 |

[a]Calculated from [$^3$H] measurement values. cpm measurement values of allergen-stimulated cell cultures/cpm measurement values of unstimulated cell cultures
[b]Donor: clinically defined grass pollen allergy sufferers The results with ten TCLs from six allergy sufferers show that these TCLs were stimulated to proliferation by Phl p 5a DM Δ94-113, 175-198 in comparable strength as by the unchanged natural or recombinant wild-type allergen (Table 3).

The present invention thus relates to variants of the group 5 allergens of the Pooideae which are characterised by reduced IgE reactivity compared with the known wild-type allergens and by retained reactivity with T-lymphocytes. These group 5 allergens are preferably Phl p 5a, Poa p 5 and Lol p 5, very particularly preferably Phl p 5a.

As it has proven particularly favourable for the purposes of the invention for amino-acid sequence regions which correspond to amino-acid sequence regions 94-113 and 175-198 of Phl p 5a to be missing or removed in the group 5 allergens, this invention relates, in particular, to such allergen variants. The first-mentioned or second-mentioned region may be missing individually, but also both said regions may be missing simultaneously, with the latter embodiment being very particularly preferred.

Owing to the high sequence homologies within the group 5 allergens from Pooideae, these regions can be unambiguously identified in sequence alignments of the Phl p 5a sequence with sequences from other group 5 allergens. The above-described allergen variants preferably originate from Phl p 5a or correspond to the sequences in accordance with SEQ ID NO 4, 6 or 8.

The allergen variants according to the invention can be prepared starting from the cloned DNA sequence with the aid of genetic engineering methods. In principle, however, chemical modifications of the native allergen extract are also possible (Fiebig, 1995, Allergo J. 4 (7), 377-382).

Naturally, further modifications in other positions—for example in order to increase the hypoallergeneity—are also possible via the variations of group 5 allergens described in the present patent application. These modifications can be, for example, amino acid insertions, deletions and exchanges, cleavage of the protein into fragments and fusion of the protein or fragments thereof with other proteins or peptides.

During preparation of the allergen variants described in more detail here, an His tag was introduced by genetic engineering methods for the purposes of improved purification of the overexpressed proteins.

The invention furthermore relates to a DNA molecule encoding for an allergen variant described above, in particular corresponding to a sequence in accordance with SEQ ID NO 3, 5 or 7, to a recombinant expression vector containing this DNA molecule, and to a host organism transformed with said DNA molecule or said expression vector. Suitable host organisms may be prokaryotic or eukaryotic, single- or multicelled organisms, such as bacteria or yeasts. A host organism which is preferred in accordance with the invention is *E. coli.*

The invention furthermore relates to a process for the preparation of an allergen variant according to the invention by cultivation of the said host organism and isolation of the corresponding allergen variant from the culture.

The present invention additionally relates to the allergen variants, DNA molecules and expression vectors described above in their property as medicaments.

The present invention furthermore relates to pharmaceutical compositions comprising at least one of these allergen variants or a corresponding DNA molecule or a corresponding expression vector and optionally further active ingredients and/or adjuvants for the treatment of allergies in the triggering of which group 5 allergens of the Pooideae are involved, or for the immunotherapeutic vaccination of patients having allergies in the triggering of which group 5 allergens of the Pooideae are involved and/or for the prevention of such allergies.

If these are pharmaceutical compositions of the second type (comprising at least one DNA molecule or an expression vector), these compositions preferably furthermore comprise aluminum hydroxide, an immunostimulatory CpG-containing oligonucleotide or a combination of the two as adjuvants.

For the purposes of this invention, pharmaceutical compositions can be used as therapeutic agents in human or veterinary medicine. Suitable excipients are organic or inorganic substances which are suitable for parenteral administration and do not react with group 5 allergen variants according to the invention. Suitable for parenteral administration are, in particular, solutions, preferably oily or aqueous solutions, furthermore suspensions, emulsions or implants. The allergen variants according to the invention may also be lyophilised and the resultant lyophilisates used, for example, for the preparation of injection preparations. The compositions indicated may be sterilised and/or comprise adjuvants, such as lubricants, preservatives, stabilisers and/or wetting agents, emulsifiers, salts for modifying the osmotic pressure, buffer substances and/or a plurality of further active ingredients.

Furthermore, appropriate formulation of the allergen variants according to the invention enables depot preparations to be obtained, for example by adsorption on aluminum hydroxide.

Finally, the present invention relates to the use of at least one allergen variant according to the invention or a DNA molecule according to the invention or an expression vector according to the invention for the preparation of a medicament for the treatment of allergies in the triggering of which group 5 allergens of the Pooideae are involved or for the immunotherapeutic vaccination of patients having allergies in the triggering of which group 5 allergens of the Pooideae are involved and/or for the prevention of such allergies.

We claim:

1. A polypeptide which comprises a polypeptide sequence selected from the group consisting of SEQ ID NO: 4, SEQ ID NO: 6 and SEQ ID NO: 8.

2. The polypeptide according to claim 1, which comprises the polypeptide sequence of SEQ ID NO: 4.

3. The polypeptide according to claim 1, which is obtained by recombinant genetic engineering methods.

4. A process for the preparation of at least one polypeptide according to claim 1 comprising culturing a host organism transformed with a DNA encoding said at least one polypeptide according to claim 1 or a vector comprising said DNA encoding said at least one polypeptide according to claim 1; and isolating the polypeptide from the culture.

5. A medicament comprising at least one polypeptide according to claim 1 and an excipient.

6. A pharmaceutical composition comprising at least one polypeptide according to claim 1 and a further active ingredient or adjuvant.

7. A method for treating an allergy triggered by a group 5 allergen of Pooideae species, comprising administering to a subject in need thereof at least one polypeptide according to claim 1.

8. The pharmaceutical composition according to claim 6, wherein the adjuvant is aluminum hydroxide, an immunostimulatory CpG-containing oligonucleotide or a combination thereof.

9. A method for the treatment of an allergy triggered by group 5 allergens of Pooideae species, comprising administering to a subject in need thereof the pharmaceutical composition according to claim 6.

10. A variant polypeptide which consists of (a) amino acids 1-37 and 58-206 of SEQ ID NO: 19;

(b) amino acids 1-118 and 143-206 of SEQ ID NO: 19; or (c) amino acids 1-37, 58-118 and 143-206 of SEQ ID NO: 19.

11. A variant polypeptide which consists of (a) amino acids 1-33 and 54-204 of SEQ ID NO: 20;

(b) amino acids 1-116 and 141-204 of SEQ ID NO: 20; or (c) amino acids 1-33, 54-116 and 141-204 of SEQ ID NO: 20.

12. A variant polypeptide which consists of (a) amino acids 1-39 and 60-208 of SEQ ID NO: 21;

(b) amino acids 1-120 and 145-208 of SEQ ID NO: 21; or (c) amino acids 1-39, 60-120 and 145-208 of SEQ ID NO: 21.

13. A variant polypeptide which consists of (a) amino acids 1-39 and 60-210 of SEQ ID NO: 22;

(b) amino acids 1-122 and 147-210 of SEQ ID NO: 22; or (c) amino acids 1-39, 60-210 and 147-210 of SEQ ID NO: 22.

14. A polypeptide according to claim 1, which is an isolated polypeptide.

* * * * *

SEQUENCE LISTING

```
<160> NUMBER OF SEQ ID NOS: 22

<210> SEQ ID NO 1
<211> LENGTH: 855
<212> TYPE: DNA
<213> ORGANISM: Phleum pratense

<400> SEQUENCE: 1

gccgatctag gctacggccc ggccacccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctcca aggccgcgct cacctccaag     300

ctcgacgccg cctacaagct cgcctacaag acagccgagg gcgcgacgcc tgaggccaag     360

tacgacgcct acgtcgccac cctaagcgag gcgctccgca tcatcgccgg caccctcgag     420

gtccacgccg tcaagcccgc ggccgaggag gtcaaggtta tccctgccgg cgagctgcag     480

gtcatcgaga aggtcgacgc cgccttcaag gtcgctgcca ccgccgccaa cgccgcgccc     540

gccaacgaca agttcaccgt cttcgaggcc gccttcaaca acgccatcaa ggcgagcacg     600
```

-continued

```
ggcggcgcct acgagagcta caagttcatc cccgccctgg aggccgccgt caagcaggcc    660

tacgccgcca ccgtcgccac cgcgccggag gtcaagtaca ccgtctttga gaccgcgctg    720

aaaaaggcca tcaccgccat gtccgaggcc cagaaggctg ccaagcccgc tgccgctgcc    780

accgccaccg caacctccgc cgttggcgcg gccaccggcg ccgccaccgc cgctactggt    840

ggctacaaag tctga                                                     855
```

```
<210> SEQ ID NO 2
<211> LENGTH: 284
<212> TYPE: PRT
<213> ORGANISM: Phleum pratense

<400> SEQUENCE: 2

Ala Asp Leu Gly Tyr Gly Pro Ala Thr Pro Ala Ala Pro Ala Ala Gly
1               5                   10                  15

Tyr Thr Pro Ala Ala Pro Ala Gly Ala Glu Pro Ala Gly Lys Ala Thr
            20                  25                  30

Thr Glu Glu Gln Lys Leu Ile Glu Lys Ile Asn Ala Gly Phe Lys Ala
        35                  40                  45

Ala Leu Ala Ala Ala Ala Gly Val Pro Pro Ala Asp Lys Tyr Arg Thr
    50                  55                  60

Phe Val Ala Thr Phe Gly Ala Ala Ser Asn Lys Ala Phe Ala Glu Gly
65                  70                  75                  80

Leu Ser Gly Glu Pro Lys Gly Ala Ala Glu Ser Ser Ser Lys Ala Ala
                85                  90                  95

Leu Thr Ser Lys Leu Asp Ala Ala Tyr Lys Leu Ala Tyr Lys Thr Ala
            100                 105                 110

Glu Gly Ala Thr Pro Glu Ala Lys Tyr Asp Ala Tyr Val Ala Thr Leu
        115                 120                 125

Ser Glu Ala Leu Arg Ile Ile Ala Gly Thr Leu Glu Val His Ala Val
    130                 135                 140

Lys Pro Ala Ala Glu Glu Val Lys Val Ile Pro Ala Gly Glu Leu Gln
145                 150                 155                 160

Val Ile Glu Lys Val Asp Ala Ala Phe Lys Val Ala Ala Thr Ala Ala
                165                 170                 175

Asn Ala Ala Pro Ala Asn Asp Lys Phe Thr Val Phe Glu Ala Ala Phe
            180                 185                 190

Asn Asn Ala Ile Lys Ala Ser Thr Gly Gly Ala Tyr Glu Ser Tyr Lys
        195                 200                 205

Phe Ile Pro Ala Leu Glu Ala Ala Val Lys Gln Ala Tyr Ala Ala Thr
    210                 215                 220

Val Ala Thr Ala Pro Glu Val Lys Tyr Thr Val Phe Glu Thr Ala Leu
225                 230                 235                 240

Lys Lys Ala Ile Thr Ala Met Ser Glu Ala Gln Lys Ala Ala Lys Pro
                245                 250                 255

Ala Ala Ala Ala Thr Ala Thr Ala Thr Ser Ala Val Gly Ala Ala Thr
            260                 265                 270

Gly Ala Ala Thr Ala Ala Thr Gly Gly Tyr Lys Val
        275                 280
```

```
<210> SEQ ID NO 3
<211> LENGTH: 795
<212> TYPE: DNA
<213> ORGANISM: Phleum pratense

<400> SEQUENCE: 3
```

```
gccgatctag gctacggccc ggccacccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctccg gcgcgacgcc tgaggccaag     300

tacgacgcct acgtcgccac cctaagcgag gcgctccgca tcatcgccgg caccctcgag     360

gtccacgccg tcaagcccgc ggccgaggag gtcaaggtta tccctgccgg cgagctgcag     420

gtcatcgaga aggtcgacgc cgccttcaag gtcgctgcca ccgccgccaa cgccgcgccc     480

gccaacgaca agttcaccgt cttcgaggcc gccttcaaca acgccatcaa ggcgagcacg     540

ggcggcgcct acgagagcta caagttcatc cccgccctgg aggccgccgt caagcaggcc     600

tacgccgcca ccgtcgccac cgcgccggag gtcaagtaca ccgtctttga gaccgcgctg     660

aaaaaggcca tcaccgccat gtccgaggcc cagaaggctg ccaagcccgc tgccgctgcc     720

accgccaccg caacctccgc cgttggcgcg gccaccggcg ccgccaccgc cgctactggt     780

ggctacaaag tctga                                                      795


<210> SEQ ID NO 4
<211> LENGTH: 264
<212> TYPE: PRT
<213> ORGANISM: Phleum pratense

<400> SEQUENCE: 4

Ala Asp Leu Gly Tyr Gly Pro Ala Thr Pro Ala Ala Pro Ala Ala Gly
1               5                   10                  15

Tyr Thr Pro Ala Ala Pro Ala Gly Ala Glu Pro Ala Gly Lys Ala Thr
            20                  25                  30

Thr Glu Glu Gln Lys Leu Ile Glu Lys Ile Asn Ala Gly Phe Lys Ala
        35                  40                  45

Ala Leu Ala Ala Ala Ala Gly Val Pro Pro Ala Asp Lys Tyr Arg Thr
    50                  55                  60

Phe Val Ala Thr Phe Gly Ala Ala Ser Asn Lys Ala Phe Ala Glu Gly
65                  70                  75                  80

Leu Ser Gly Glu Pro Lys Gly Ala Ala Glu Ser Ser Ser Gly Ala Thr
                85                  90                  95

Pro Glu Ala Lys Tyr Asp Ala Tyr Val Ala Thr Leu Ser Glu Ala Leu
            100                 105                 110

Arg Ile Ile Ala Gly Thr Leu Glu Val His Ala Val Lys Pro Ala Ala
        115                 120                 125

Glu Glu Val Lys Val Ile Pro Ala Gly Glu Leu Gln Val Ile Glu Lys
    130                 135                 140

Val Asp Ala Ala Phe Lys Val Ala Ala Thr Ala Ala Asn Ala Ala Pro
145                 150                 155                 160

Ala Asn Asp Lys Phe Thr Val Phe Glu Ala Ala Phe Asn Asn Ala Ile
                165                 170                 175

Lys Ala Ser Thr Gly Gly Ala Tyr Glu Ser Tyr Lys Phe Ile Pro Ala
            180                 185                 190

Leu Glu Ala Ala Val Lys Gln Ala Tyr Ala Ala Thr Val Ala Thr Ala
        195                 200                 205

Pro Glu Val Lys Tyr Thr Val Phe Glu Thr Ala Leu Lys Lys Ala Ile
    210                 215                 220

Thr Ala Met Ser Glu Ala Gln Lys Ala Ala Lys Pro Ala Ala Ala Ala
225                 230                 235                 240
```

```
Thr Ala Thr Ala Thr Ser Ala Val Gly Ala Ala Thr Gly Ala Ala Thr
                245                 250                 255

Ala Ala Thr Gly Gly Tyr Lys Val
            260
```

```
<210> SEQ ID NO 5
<211> LENGTH: 783
<212> TYPE: DNA
<213> ORGANISM: Phleum pratense

<400> SEQUENCE: 5

gccgatctag gctacggccc ggccacccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctcca aggccgcgct cacctccaag     300

ctcgacgccg cctacaagct cgcctacaag acagccgagg gcgcgacgcc tgaggccaag     360

tacgacgcct acgtcgccac cctaagcgag gcgctccgca tcatcgccgg caccctcgag     420

gtccacgccg tcaagcccgc ggccgaggag gtcaaggtta tccctgccgg cgagctgcag     480

gtcatcgaga aggtcgacgc cgccttcaag gtcgctgcca ccagcacggg cggcgcctac     540

gagagctaca agttcatccc cgccctggag gccgccgtca agcaggccta cgccgccacc     600

gtcgccaccg cgccggaggt caagtacacc gtctttgaga ccgcgctgaa aaaggccatc     660

accgccatgt ccgaggccca gaaggctgcc aagcccgctg ccgctgccac cgccaccgca     720

acctccgccg ttggcgcggc caccggcgcc gccaccgccg ctactggtgg ctacaaagtc     780

tga                                                                   783
```

```
<210> SEQ ID NO 6
<211> LENGTH: 260
<212> TYPE: PRT
<213> ORGANISM: Phleum pratense

<400> SEQUENCE: 6

Ala Asp Leu Gly Tyr Gly Pro Ala Thr Pro Ala Ala Pro Ala Ala Gly
1               5                   10                  15

Tyr Thr Pro Ala Ala Pro Ala Gly Ala Glu Pro Ala Gly Lys Ala Thr
            20                  25                  30

Thr Glu Glu Gln Lys Leu Ile Glu Lys Ile Asn Ala Gly Phe Lys Ala
        35                  40                  45

Ala Leu Ala Ala Ala Ala Gly Val Pro Pro Ala Asp Lys Tyr Arg Thr
    50                  55                  60

Phe Val Ala Thr Phe Gly Ala Ala Ser Asn Lys Ala Phe Ala Glu Gly
65                  70                  75                  80

Leu Ser Gly Glu Pro Lys Gly Ala Ala Glu Ser Ser Ser Lys Ala Ala
                85                  90                  95

Leu Thr Ser Lys Leu Asp Ala Ala Tyr Lys Leu Ala Tyr Lys Thr Ala
            100                 105                 110

Glu Gly Ala Thr Pro Glu Ala Lys Tyr Asp Ala Tyr Val Ala Thr Leu
        115                 120                 125

Ser Glu Ala Leu Arg Ile Ile Ala Gly Thr Leu Glu Val His Ala Val
    130                 135                 140

Lys Pro Ala Ala Glu Glu Val Lys Val Ile Pro Ala Gly Glu Leu Gln
145                 150                 155                 160
```

```
Val Ile Glu Lys Val Asp Ala Ala Phe Lys Val Ala Ala Thr Ser Thr
                165                 170                 175

Gly Gly Ala Tyr Glu Ser Tyr Lys Phe Ile Pro Ala Leu Glu Ala Ala
            180                 185                 190

Val Lys Gln Ala Tyr Ala Ala Thr Val Ala Thr Ala Pro Glu Val Lys
        195                 200                 205

Tyr Thr Val Phe Glu Thr Ala Leu Lys Lys Ala Ile Thr Ala Met Ser
    210                 215                 220

Glu Ala Gln Lys Ala Ala Lys Pro Ala Ala Ala Ala Thr Ala Thr Ala
225                 230                 235                 240

Thr Ser Ala Val Gly Ala Ala Thr Gly Ala Ala Thr Ala Ala Thr Gly
                245                 250                 255

Gly Tyr Lys Val
        260
```

<210> SEQ ID NO 7
<211> LENGTH: 723
<212> TYPE: DNA
<213> ORGANISM: Phleum pratense

<400> SEQUENCE: 7

```
gccgatctag gctacggccc ggccaccccca gctgccccgg ccgccggcta cacccccgcc      60

gccccggccg gagcggagcc agcaggtaag gcgacgaccg aggagcagaa gctgatcgag     120

aagatcaacg ccggcttcaa ggcggccttg gccgctgccg ccggcgtccc gccagcggac     180

aagtacagga cgttcgtcgc aaccttcggc gcggcctcca acaaggcctt cgcggagggc     240

ctctcgggcg agcccaaggg cgccgccgaa tccagctccg gcgcgacgcc tgaggccaag     300

tacgacgcct acgtcgccac cctaagcgag gcgctccgca tcatcgccgg caccctcgag     360

gtccacgccg tcaagcccgc ggccgaggag gtcaaggtta tccctgccgg cgagctgcag     420

gtcatcgaga aggtcgacgc cgccttcaag gtcgctgcca ccagcacggg cggcgcctac     480

gagagctaca agttcatccc cgccctggag gccgccgtca agcaggccta cgccgccacc     540

gtcgccaccg cgccggaggt caagtacacc gtctttgaga ccgcgctgaa aaaggccatc     600

accgccatgt ccgaggccca gaaggctgcc aagcccgctg ccgctgccac cgccaccgca     660

acctccgccg ttggcgcggc caccggcgcc gccaccgccg ctactggtgg ctacaaagtc     720

tga                                                                   723
```

<210> SEQ ID NO 8
<211> LENGTH: 240
<212> TYPE: PRT
<213> ORGANISM: Phleum pratense

<400> SEQUENCE: 8

```
Ala Asp Leu Gly Tyr Gly Pro Ala Thr Pro Ala Ala Pro Ala Ala Gly
1               5                   10                  15

Tyr Thr Pro Ala Ala Pro Ala Gly Ala Glu Pro Ala Gly Lys Ala Thr
            20                  25                  30

Thr Glu Glu Gln Lys Leu Ile Glu Lys Ile Asn Ala Gly Phe Lys Ala
        35                  40                  45

Ala Leu Ala Ala Ala Ala Gly Val Pro Pro Ala Asp Lys Tyr Arg Thr
    50                  55                  60

Phe Val Ala Thr Phe Gly Ala Ala Ser Asn Lys Ala Phe Ala Glu Gly
65                  70                  75                  80

Leu Ser Gly Glu Pro Lys Gly Ala Ala Glu Ser Ser Ser Gly Ala Thr
```

-continued

```
                85                  90                  95

Pro Glu Ala Lys Tyr Asp Ala Tyr Val Ala Thr Leu Ser Glu Ala Leu
            100                 105                 110

Arg Ile Ile Ala Gly Thr Leu Glu Val His Ala Val Lys Pro Ala Ala
        115                 120                 125

Glu Glu Val Lys Val Ile Pro Ala Gly Glu Leu Gln Val Ile Glu Lys
    130                 135                 140

Val Asp Ala Ala Phe Lys Val Ala Ala Thr Ser Thr Gly Gly Ala Tyr
145                 150                 155                 160

Glu Ser Tyr Lys Phe Ile Pro Ala Leu Glu Ala Ala Val Lys Gln Ala
                165                 170                 175

Tyr Ala Ala Thr Val Ala Thr Ala Pro Glu Val Lys Tyr Thr Val Phe
            180                 185                 190

Glu Thr Ala Leu Lys Lys Ala Ile Thr Ala Met Ser Glu Ala Gln Lys
        195                 200                 205

Ala Ala Lys Pro Ala Ala Ala Ala Thr Ala Thr Ala Thr Ser Ala Val
    210                 215                 220

Gly Ala Ala Thr Gly Ala Ala Thr Ala Ala Thr Gly Gly Tyr Lys Val
225                 230                 235                 240


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gccgatctag gctacggccc ggcc                                            24


<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

aacataacta gtggcagcga ccttgaaggc ggcgtc                               36


<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

atctaactag tacgggcggc gcctacgaga                                      30


<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

aacataaagc tttcagactt tgtagccacc agt                                  33
```

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggagctggat tcggcggcgc ccttggg 27

<210> SEQ ID NO 14
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gccgccgaat ccagctccgg cgcgacgcct gaggccaagt acgac 45

<210> SEQ ID NO 15
<211> LENGTH: 375
<212> TYPE: DNA
<213> ORGANISM: Poa pratensis

<400> SEQUENCE: 15
gccgccgtag acagctccaa ggccgcgctc acctccaagc tcgacgccgc ctacaagctc 60
gcctacaagt cagccgaggg cgcgacgccc gaggctaagt acgacgacta cgtcgccacc 120
cttagcgagg ccctccgcat cattgccggc accctcgagg tccacggcgt caagcccgcg 180
gccgaggagg tcaaggccac ccccgccggc gagctccagg tcatcgacaa ggtcgacgcc 240
gccttcaagg tcgctgccac cgccgccaac gccgcccccg ccaacgacaa gttcaccgtc 300
ttcgaggccg ccttcaacga tgccatcaag gcgagcacgg gcggcgccta ccagagctac 360
aagttcatcc ccgcc 375

<210> SEQ ID NO 16
<211> LENGTH: 382
<212> TYPE: DNA
<213> ORGANISM: Lolium perenne

<400> SEQUENCE: 16
ggctacgccg atcaaagcaa gaaccagctc acctccaagc tcgacgccgc cttaaagcct 60
cgcttacgag gctgcccagg gcgccactcc cgaggccaag tacgatgcct acgtcgccac 120
cctcaccgag gcgctccgcg tcatcgccgg caccctcgag gtccacgccg taaagcccgc 180
cgccgaggag gtcaaggtcg gcgccatccc cgccgccgag gtgcagctca tcgacaaggt 240
cgacgccgcg tacaggaccg ccgccactgc cgccaacgcc gcccccgcca acgacaagtt 300
caccgtcttc gagaacacct ttaacaatgc catcaaggtg agcctgggcg ccgcctacga 360
cagctacaag ttcatcccca cc 382

<210> SEQ ID NO 17
<211> LENGTH: 378
<212> TYPE: DNA
<213> ORGANISM: Hordeum vulgare

<400> SEQUENCE: 17
gatcgccggc cagtccagct ccatggccaa actctccagc agcctcgaac tctcctacaa 60
gctcgcctac gacaaagccc agggcgccac cccgaggcca agtacgacgc ctacgtcgcc 120
accctcaccg agtcgctccg cgtcatctcc ggcaccctcg aggtccactc cgtcaagccc 180
gccgccgagg aggttaaggg cgtccccgcc ggcgagctga aggccattga ccaggtcgac 240
gccgccttca ggaccgccgc caccgccgct gacgctgccc cggccaacga caagttcacc 300
gtcttcgagt cgcttcaaca aggtccatca aggaaaccac ggggcggcgc gtacgagagt 360
tacaagttca tccccgcc 378

<210> SEQ ID NO 18
<211> LENGTH: 379
<212> TYPE: DNA
<213> ORGANISM: Triticum aestivum

<400> SEQUENCE: 18
gatgcccgcc cagtcagcct ccatggcatc actctccaag agcctcgaag cctcctacaa 60
gctcgcctac gacaaagccc agggcgccac ccccgagacc aagtacgaca cctacgtcgc 120
cagtctcacc gagtcgctcc gcgtcatctc cggcgccttc gaggtccact ccgtcaagcc 180
cgccgccgag gaggtcaagg ggatccccgc cccccagctc aagaccatcg accagatcga 240
cgccgcctac aggaccgccg ccaccgccgc cgacgctgcc ccggtcaacg acaagttcac 300
cgtcttcgag tccgccttca acaaggccat caaggagacc acgggcggcg catacgacaa 360
ctacaagttc gtccccgcc 379

<210> SEQ ID NO 19
<211> LENGTH: 206
<212> TYPE: PRT
<213> ORGANISM: Poa pratensis

<400> SEQUENCE: 19

Pro Ala Ala Asn Lys Tyr Lys Thr Phe Val Ala Thr Phe Gly Ala Ala
1 5 10 15

Ser Asn Lys Ala Phe Ala Glu Ala Leu Ser Thr Glu Pro Lys Gly Ala
20 25 30

Ala Val Asp Ser Ser Lys Ala Ala Leu Thr Ser Lys Leu Asp Ala Ala
35 40 45

Tyr Lys Leu Ala Tyr Lys Ser Ala Glu Gly Ala Thr Pro Glu Ala Lys
50 55 60

Tyr Asp Asp Tyr Val Ala Thr Leu Ser Glu Ala Leu Arg Ile Ile Ala
65 70 75 80

Gly Thr Leu Glu Val His Gly Val Lys Pro Ala Ala Glu Glu Val Lys
85 90 95

Ala Thr Pro Ala Gly Glu Leu Gln Val Ile Asp Lys Val Asp Ala Ala
100 105 110

Phe Lys Val Ala Ala Thr Ala Ala Asn Ala Ala Pro Ala Asn Asp Lys
115 120 125

Phe Thr Val Phe Glu Ala Ala Phe Asn Asp Ala Ile Lys Ala Ser Thr
130 135 140

Gly Gly Ala Tyr Gln Ser Tyr Lys Phe Ile Pro Ala Leu Glu Ala Ala
145 150 155 160

Val Lys Gln Ser Tyr Ala Ala Thr Val Ala Thr Ala Pro Ala Val Lys
165 170 175

Tyr Thr Val Phe Glu Thr Ala Leu Lys Lys Ala Ile Thr Ala Met Ser
180 185 190

Gln Ala Gln Lys Ala Ala Lys Pro Ala Ala Ala Ala Thr Gly

-continued 195 200 205

<210> SEQ ID NO 20
<211> LENGTH: 204
<212> TYPE: PRT
<213> ORGANISM: Lolium perenne

<400> SEQUENCE: 20

Pro Pro Ala Asp Lys Tyr Lys Thr Phe Val Glu Thr Phe Gly Thr Ala
1 5 10 15

Thr Asn Lys Ala Phe Val Glu Gly Leu Ala Ser Gly Tyr Ala Asp Gln
20 25 30

Ser Lys Asn Gln Leu Thr Ser Lys Leu Asp Ala Ala Leu Lys Leu Ala
35 40 45

Tyr Glu Ala Ala Gln Gly Ala Thr Pro Glu Ala Lys Tyr Asp Ala Tyr
50 55 60

Val Ala Thr Leu Thr Glu Ala Leu Arg Val Ile Ala Gly Thr Leu Glu
65 70 75 80

Val His Ala Val Lys Pro Ala Ala Glu Glu Val Lys Val Gly Ala Ile
85 90 95

Pro Ala Ala Glu Val Gln Leu Ile Asp Lys Val Asp Ala Ala Tyr Arg
100 105 110

Thr Ala Ala Thr Ala Ala Asn Ala Ala Pro Ala Asn Asp Lys Phe Thr
115 120 125

Val Phe Glu Asn Thr Phe Asn Asn Ala Ile Lys Val Ser Leu Gly Ala
130 135 140

Ala Tyr Asp Ser Tyr Lys Phe Ile Pro Thr Leu Val Ala Ala Val Lys
145 150 155 160

Gln Ala Tyr Ala Ala Lys Gln Ala Thr Ala Pro Glu Val Lys Tyr Thr
165 170 175

Val Ser Glu Thr Ala Leu Lys Lys Ala Val Thr Ala Met Ser Glu Ala
180 185 190

Glu Lys Glu Ala Thr Pro Ala Ala Ala Ala Thr Ala
195 200

<210> SEQ ID NO 21
<211> LENGTH: 208
<212> TYPE: PRT
<213> ORGANISM: Hordeum vulgare

<400> SEQUENCE: 21

Pro Pro Ala Asp Lys Tyr Lys Thr Phe Glu Ala Thr Phe Ala Ala Ala
1 5 10 15

Ser Asn Lys Ala Phe Ala Glu Val Leu Lys Gly Ala Ala Thr Gly Gln
20 25 30

Ile Ala Gly Gln Ser Ser Ser Met Ala Lys Leu Ser Ser Ser Leu Glu
35 40 45

Leu Ser Tyr Lys Leu Ala Tyr Asp Lys Ala Gln Gly Ala Thr Pro Glu
50 55 60

Ala Lys Tyr Asp Ala Tyr Val Ala Thr Leu Thr Glu Ser Leu Arg Val
65 70 75 80

Ile Ser Gly Thr Leu Glu Val His Ser Val Lys Pro Ala Ala Glu Glu
85 90 95

Val Lys Gly Val Pro Ala Gly Glu Leu Lys Ala Ile Asp Gln Val Asp
100 105 110

Ala Ala Phe Arg Thr Ala Ala Thr Ala Ala Asp Ala Ala Pro Ala Asn
115 120 125

```
Asp Lys Phe Thr Val Phe Glu Ser Leu Gln Gln Gly Pro Ser Arg Lys
    130                 135                 140

Pro Arg Gly Gly Ala Tyr Glu Ser Tyr Lys Phe Ile Pro Ala Leu Glu
145                 150                 155                 160

Ala Ala Val Lys Gln Ala Tyr Ala Ala Thr Val Ala Ala Ala Pro Glu
                165                 170                 175

Val Lys Phe Thr Val Phe Gln Thr Ala Leu Ser Lys Ala Ile Asn Ala
            180                 185                 190

Met Thr Gln Ala Gly Lys Val Ala Lys Pro Ala Ala Ala Ala Thr Ala
        195                 200                 205


<210> SEQ ID NO 22
<211> LENGTH: 210
<212> TYPE: PRT
<213> ORGANISM: Triticum aestivum
<220> FEATURE:
<221> NAME/KEY: MOD_RES
<222> LOCATION: (19)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid

<400> SEQUENCE: 22

Pro Pro Ala Asp Lys Tyr Lys Thr Phe Glu Ala Thr Phe Ser Ala Ala
1               5                   10                  15

Ser Asn Xaa Ala Phe Ala Asp Val Leu Lys Ala Ala Ala Ser Gly Gln
            20                  25                  30

Met Pro Ala Gln Ser Ala Ser Met Ala Ser Leu Ser Lys Ser Leu Glu
        35                  40                  45

Ala Ser Tyr Lys Leu Ala Tyr Asp Lys Ala Gln Gly Ala Thr Pro Glu
    50                  55                  60

Thr Lys Tyr Asp Thr Tyr Val Ala Ser Leu Thr Glu Ser Leu Arg Val
65                  70                  75                  80

Ile Ser Gly Ala Phe Glu Val His Ser Val Lys Pro Ala Ala Glu Glu
                85                  90                  95

Val Lys Gly Xaa Xaa Ile Pro Ala Pro Gln Leu Lys Thr Ile Asp Gln
            100                 105                 110

Ile Asp Ala Ala Tyr Arg Thr Ala Ala Thr Ala Ala Asp Ala Ala Pro
        115                 120                 125

Val Asn Asp Lys Phe Thr Val Phe Glu Ser Ala Phe Asn Lys Ala Ile
    130                 135                 140

Lys Glu Thr Thr Gly Gly Ala Tyr Asp Asn Tyr Lys Phe Val Pro Ala
145                 150                 155                 160

Leu Glu Ser Ala Val Lys Gln Ala Tyr Ala Ala Thr Val Ala Ser Ala
                165                 170                 175

Pro Glu Val Lys Tyr Ala Val Phe Gln Ala Ala Leu Ser Lys Ala Ile
            180                 185                 190

Asn Ala Met Val Glu Ala Glu Lys Asp Ala Gly Ala Ala Ala Ala Gly
        195                 200                 205

Gly Tyr
    210
```